US012350455B2

(12) United States Patent
Soverow

(10) Patent No.: US 12,350,455 B2
(45) Date of Patent: Jul. 8, 2025

(54) ANGIOPLASTY BALLOON SNARE

(71) Applicant: Jonathan Soverow, McLean, VA (US)

(72) Inventor: Jonathan Soverow, McLean, VA (US)

( * ) Notice: Subject to any disclaimer, the term of this patent is extended or adjusted under 35 U.S.C. 154(b) by 1340 days.

(21) Appl. No.: 16/602,054

(22) Filed: Jul. 24, 2019

(65) Prior Publication Data
US 2020/0069923 A1 Mar. 5, 2020

Related U.S. Application Data

(60) Provisional application No. 62/765,509, filed on Aug. 29, 2018.

(51) Int. Cl.
*A61M 25/10* (2013.01)

(52) U.S. Cl.
CPC ... *A61M 25/104* (2013.01); *A61M 2025/1056* (2013.01); *A61M 2025/1079* (2013.01); *A61M 2025/109* (2013.01)

(58) Field of Classification Search
CPC ........ A61M 25/104; A61M 2025/1056; A61M 2025/109; A61M 2025/1079; A61M 2017/00358; A61M 25/1002; A61M 2025/1043; A61M 2025/1084; A61M 25/10; A61M 25/0169; A61M 25/0032; A61M 2025/1095; A61M 2025/1097; A61M 2025/1086; A61M 25/09041; A61M 25/09; A61B 2017/00358; A61B 2017/00557; A61B 17/22032;
(Continued)

(56) References Cited

U.S. PATENT DOCUMENTS 4,944,745 A 7/1990 Sogard et al.
5,192,296 A * 3/1993 Bhate ................ A61M 25/1006
604/103.07
(Continued)

FOREIGN PATENT DOCUMENTS

CN 102665578 A 9/2012

OTHER PUBLICATIONS

"Precutaneous Retrieval . . . Using a Balloon;" Gupta et al, PMCID: PMC3399715; Published on-line Oct. 25, 2005, 11 pages.
(Continued)

*Primary Examiner* — Katherine H Schwiker
*Assistant Examiner* — Lauren Dubose

(57) ABSTRACT

A snare particularly desirable for removing retrograde wires from blood vessels includes a rail wire attached to an inflatable/collapsible balloon of biocompatible semi-compliant resilient plastic material in a "fixed wire" configuration, or the balloon has a "rapid exchange" or "over-the-wire" lumen upon which the balloon may ride along a separate guide wire already in place. An additional lumen or cavity is defined by or within the balloon allowing the capture of objects, such as retrograde wires, within the lumen or cavity when the balloon is deflated. Desirably a central lumen is defined by biocompatible semi-compliant plastic material, or the balloon has a pair of arms so that a bridge wire extending between the pair of arms defines a cavity which can receive objects. An object for repositioning or removal is captured by the gripping action of the balloon assembly alone, without need for the utilization of a conventional snare.

11 Claims, 3 Drawing Sheets

(58) Field of Classification Search
CPC .. A61B 2017/22038; A61B 2017/2215; A61B 2017/22035; A61B 1/018; A61B 17/221; A61B 2017/3486
USPC .................................................. 606/194, 104
See application file for complete search history.

(56) References Cited

U.S. PATENT DOCUMENTS

| | | | | |
|---|---|---|---|---|
| 5,613,948 | A | * | 3/1997 | Avellanet ............ A61M 25/104 604/103.07 |
| 5,697,936 | A | | 12/1997 | Shipko et al. |
| 5,769,814 | A | * | 6/1998 | Wijay ................. A61M 25/003 604/103.1 |
| 6,007,517 | A | * | 12/1999 | Anderson ........... A61M 25/104 604/103.04 |
| 6,013,190 | A | | 1/2000 | Berg et al. |
| 6,056,721 | A | * | 5/2000 | Shulze .............. A61M 25/0032 600/191 |
| 6,506,180 | B1 | * | 1/2003 | Lary .................... A61M 25/104 604/101.04 |
| 6,554,842 | B2 | | 4/2003 | Heuser et al. |
| 6,960,186 | B1 | * | 11/2005 | Fukaya ............. A61M 25/1027 604/103.06 |
| 7,041,116 | B2 | * | 5/2006 | Goto ................... A61B 17/221 606/200 |
| 9,060,763 | B2 | | 6/2015 | Sengun |
| 10,010,437 | B2 | | 7/2018 | Bliss et al. |
| 2002/0161377 | A1 | | 10/2002 | Rabkin |
| 2005/0267596 | A1 | * | 12/2005 | Chen ..................... A61F 5/0033 623/23.67 |
| 2006/0074437 | A1 | * | 4/2006 | Teague ............ A61B 17/22032 606/113 |
| 2006/0241345 | A1 | * | 10/2006 | Oishi ................. A61B 17/3403 600/116 |
| 2006/0253190 | A1 | | 11/2006 | Kuo |
| 2008/0208309 | A1 | | 8/2008 | Saeed |
| 2009/0234283 | A1 | * | 9/2009 | Burton ........... A61B 17/320725 604/103.08 |
| 2013/0123621 | A1 | * | 5/2013 | Isham .................. A61N 5/1049 600/435 |
| 2013/0178888 | A1 | * | 7/2013 | Bliss ........................ A61F 2/95 606/200 |
| 2014/0364835 | A1 | * | 12/2014 | Allen ................ A61M 25/0068 604/509 |
| 2015/0112130 | A1 | * | 4/2015 | Shepherd ................. A61B 1/32 600/207 |
| 2016/0089254 | A1 | * | 3/2016 | Hopkinson ........... A61L 29/085 623/1.11 |
| 2016/0279393 | A1 | * | 9/2016 | Anderson ........ A61B 17/22032 |
| 2017/0135699 | A1 | * | 5/2017 | Wolf ..................... A61M 25/09 |
| 2018/0093079 | A1 | * | 4/2018 | Fox ..................... A61M 25/104 |
| 2021/0369185 | A1 | * | 12/2021 | Janssen ............. A61M 25/1002 |

OTHER PUBLICATIONS

Foreign Body Retrieval, https://radiologykey.com/foreign-body-retrieval./ Chapter 107, Dec. 23, 2015, 6 pages (see pp. 5 & 6).
"A novel 'balloon/snare apparatus' technique . . . " Kumbhari et al, Sep. 2016, https://www.giejournal.org/article/S0016-5107(16)30009-8/fulltext.

* cited by examiner

ANGIOPLASTY BALLOON SNARE

CROSS-REFERENCE TO RELATED APPLICATION

This application is based upon and claims the priority of U.S. Provisional Application Ser. 62/765,509 filed Aug. 29, 2018, the disclosure of which is incorporated by reference herein.

FIELD OF THE INVENTION

The invention relates to snares used during intravascular interventions or the like, including, but not limited to, the expansion via either angioplasty or stenting, of a stenotic segment of the vessel, or for the purpose of retrieving intravascular material.

BACKGROUND AND SUMMARY OF THE INVENTION

Stenotic lesions in a blood vessel, whether it be artery or vein, present risks of diminished blood flow and circulation to the target of that vessel. Multiple techniques have been developed to expand such stenotic lesions, including but not limited to angioplasty (expansion of a pressured balloon at the stenosis), atherectomy (removal of plaque from the arterial wall via mechanical means), and stenting (use of a metal cage to expand and maintain patency of the vessel lumen). Each of these techniques typically requires passage of a wire through the narrowing; the aforementioned equipment is then advanced along that wire, which acts as a rail, to the therapeutic target.

At times, crossing the lesion with the wire requires an alternate approach as the lesion characteristics may facilitate passage via a backwards, retrograde, or non-traditional vantage. Once the wire crosses from this alternate passage, however, it is still typically easiest to advance equipment over the wire from the traditional approach; thus the wire is often captured using a wire snare device and pulled backwards outside the body. Once exposed, or "externalized", the wire may then be used to advance equipment in a traditional fashion (typically antegrade), avoiding damage to the narrow, circuitous, alternate path that the wire originally took.

Conventional wire based snares are cumbersome, however, and require extensive manipulation and trial and error to capture the wire. They do not perform well in the small vessel spaces the wire typically occupies and are exceedingly difficult to use in large vessels such as the aorta.

The invention makes several novel modifications to an angioplasty balloon, which is a device which already does operate well in small vessel spaces, in order to use it as a snare to capture the wire. Angioplasty balloons typically have two lumen, one which is used to ride along a wire, and a second which is used for inflation of the balloon itself. These proposed modifications to the balloon will create an additional lumen either inside or adjacent to the balloon which, when the balloon is fully expanded, will allow easy advancement of the wire through it, and which, when collapsed/deflated, will alone (without another snare or any other device) grip the wire with sufficient force to allow the wire to be moved as desired, including for externalization.

The invention solves one of the challenges of other snare designs, wherein the material or wire often travels beside rather than within the snare, forcing the operator to undergo extensive manipulation and multiple attempts to capture the target material. The balloon's soft outer shell also has a lower propensity to damage the inner lining of the blood vessel than the more common wire-based snare designs, such as gooseneck snares. Also, the balloon's ability to obstruct the vessel (e. g. blood vessel) lumen allows easy direction of the material or wire to the only available path: the balloon's lumen or cavity.

According to one aspect of the invention there is provided a method of removing or re-positioning objects from or within a human or animal body part using a snare comprising a rail wire attached to an inflatable/collapsible balloon of biocompatible semi-compliant resilient plastic material and a lumen or cavity defined by or within the balloon allowing the capture of objects within the lumen or cavity when the balloon is deflated. The method comprises: a) advancing the snare with the balloon to a location proximate the desired object; b) if not already inflated in a), inflating the balloon to reveal the central lumen or cavity; c) moving the desired object and inflated balloon with respect to each other so that the desired object significantly enters the lumen or cavity; d) deflating the balloon so that it grips the desired object sufficiently, by itself, to allow withdrawal of the object from or re-positioning within the body part using the snare; and e) withdrawing or repositioning the balloon, with snared object, from or within the body part. In the method a)-e) may be practiced where the body part is a blood vessel, and a)-e) may be further practiced where the desired object is a retrograde wire with an end adjacent a stenosis, According to another aspect of the invention there is provided a snare comprising a rail wire attached to an inflatable/collapsible balloon of biocompatible semi-compliant resilient plastic material and a lumen or cavity defined by or within the balloon allowing the capture of objects within the lumen or cavity when the balloon is deflated. In one embodiment the balloon has a central lumen defined by biocompatible semi-compliant plastic material. In another. embodiment, the balloon has a pair of arms, and a bridge wire extending between the pair of arms defines a cavity which can receive objects.

According to another aspect of the invention there is provided a snare comprising an antegrade rail wire attached to an inflatable/collapsible balloon of biocompatible semi-compliant resilient plastic material, and wherein the balloon has a pair of arms and a bridge wire extending between the pair of arms which define a cavity which can receive an object within the cavity when the balloon is deflated and thereby grip the object sufficiently, by itself, to allow movement of the object with the balloon.

While the invention is particularly applicable to capturing a retrograde wire in a blood vessel with an angioplasty balloon snare, it has broader applicability and can be used to remove or reposition many types of objects from many different locations within a human or animal body.

DETAILED DESCRIPTION OF THE DRAWINGS

Figure 1:
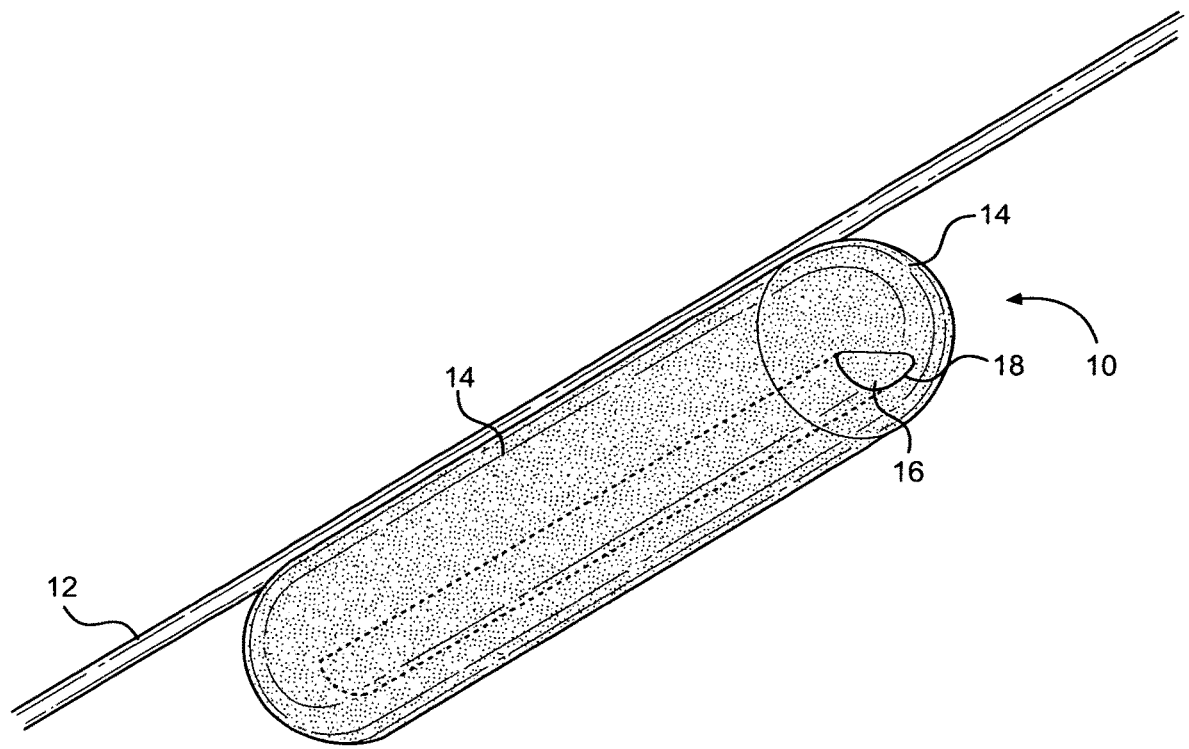
FIG. 1 is a schematic perspective view of a first embodiment of an exemplary balloon snare according to the invention.
Figure 2:
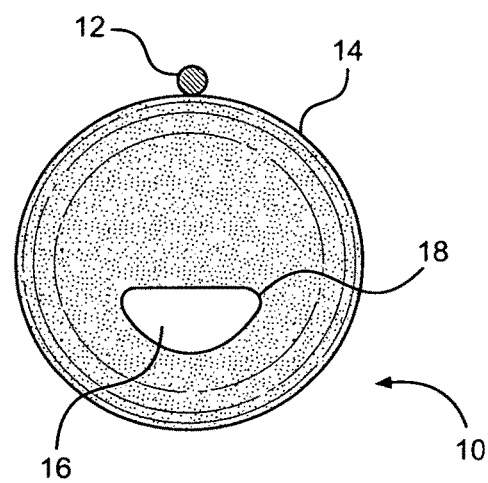
FIG. 2 is a schematic cross-sectional view of the snare of FIG. 1.

A first embodiment of an angioplasty balloon snare according to the invention is illustrated schematically at 10 in FIGS. 1 & 2. The major components include an antigrade rail wire 12 and a balloon 14 (shown in inflated/expanded condition), the balloon 14 including a central lumen 16 defined by material 18 particularly dimensioned to properly receive objects desired to be moved thereby, such as a retrograde wire. The antegrade rail wire 12 may be connected to the balloon 14 by any suitable means, such as a biocompatible adhesive or stitching in a fixed balloon design, or the balloon may ride freely along the wire as it does during standard intravascular interventions either in rapid-exchange (where only a small rail from the balloon catheter rides on the wire) or over-the-wire configuration (where the entire length of the balloon catheter is riding over the wire). The balloon 14, and the material 18 defining the lumen 16, are made of a biocompatible semi-compliant plastic resilient material having sufficient gripping power once the balloon 14 is deflated to alone (without any need for an additional snare or other device) hold an object to be moved, such as a retrograde wire, to allow its re-positioning or removal. Some non-limiting examples of such semi-compliant plastic resilient materials include nylon (polyamide), Pebax® (rigid polyamide blocks and soft polyether blocks), polyethylene terephthalate (PET), or various polyurethanes, in biocompatible form.

The lumen 16 may have a wide variety of cross-sectional dimensions and lengths. For example (only) the lumen 16 may have a cross-sectional area of about 0.005-0.50 in$^2$, and a length of about 1-600 mm. The lumen 16 desirably has the modified crescent cross-sectional shape illustrated in FIG. 2, however it may have a variety of other shapes, including circular or elliptical or approximations thereof.

The balloon 14 is connected up to conventional equipment (not shown) for inflating and deflating it. The balloon 14 may have a cross-sectional area (including the lumen 16) of about 1-80 min$^2$ and typically the same, or approximately the same, length as the lumen 16.

The material 18 defining lumen 16 may include conventional radiopaque elements to improve visualization. The material 18 defining the central lumen 16 may include a hydrophilic or hydrophobic interior coating, and the material 18 defining the lumen 16 may be simply stitched into the shape of the balloon 14 using the same material as the balloon 14.

Figure 3:
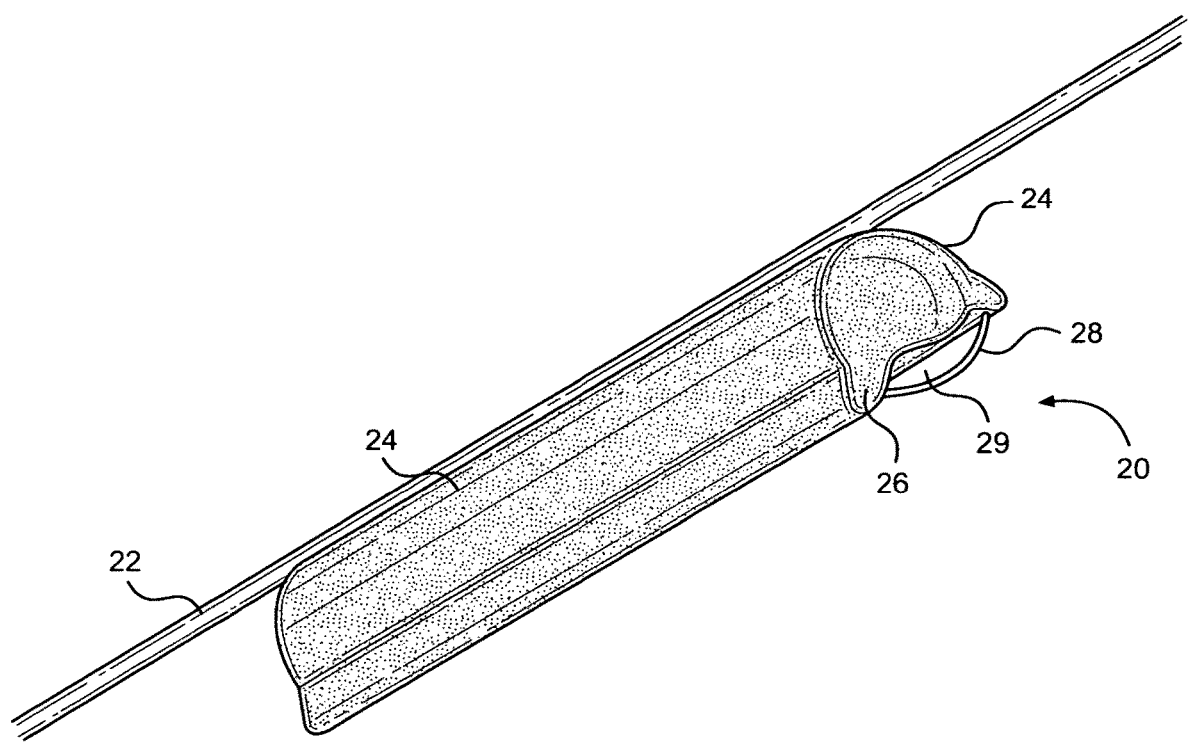
FIG. 3 is a schematic perspective view of a second embodiment of an exemplary balloon snare according to the invention.
Figure 4:
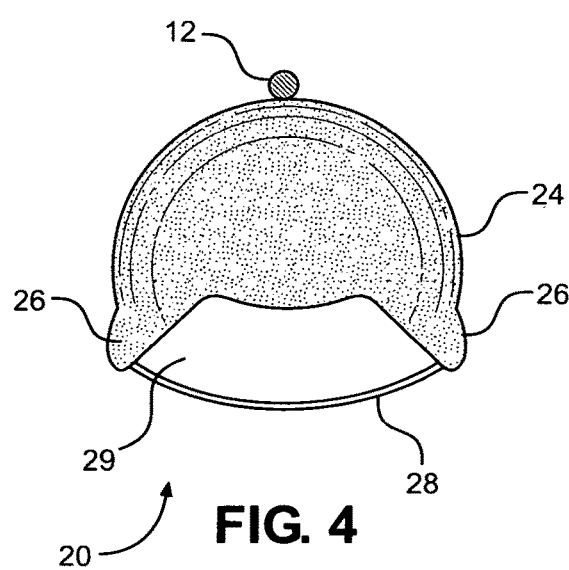
FIG. 4 is a schematic cross-sectional view of the snare of FIG. 3.

The second snare embodiment shown schematically in FIGS. 3 & 4 is indicated generally by the reference numeral 20, and comprises a rail wire 22 and a balloon 24 having a non-circular cross-section, the balloon 24 shown in inflated condition. The balloon 24 (preferably of the same materials and rough dimensions as the first embodiment of FIGS. 1 & 2) has arms 26. A capturing structure in the form of cavity 29 (comparable to the lumen 16 in the first embodiment) is defined by a bridge wire 28 extending between the arms 26. The material defining the arms 26 may include conventional radiopaque elements to improve visualization. The balloon 24 is connected to the same type of conventional equipment (not shown) for inflating and deflating it as is the balloon 14.

The bridge wire 28 may be made of any suitable material, and a plurality of such wires may be provided depending upon the length of the cavity 29. One exemplary material for the bridge wire 28 is a corrosion-proof metal (such as stainless steel, nitinol, platinum, silver, or gold). The wire 28 may have a diameter (or comparable cross-sectional area if not circular in cross-section) of about 0.005-0.5 mm.

Figure 5:
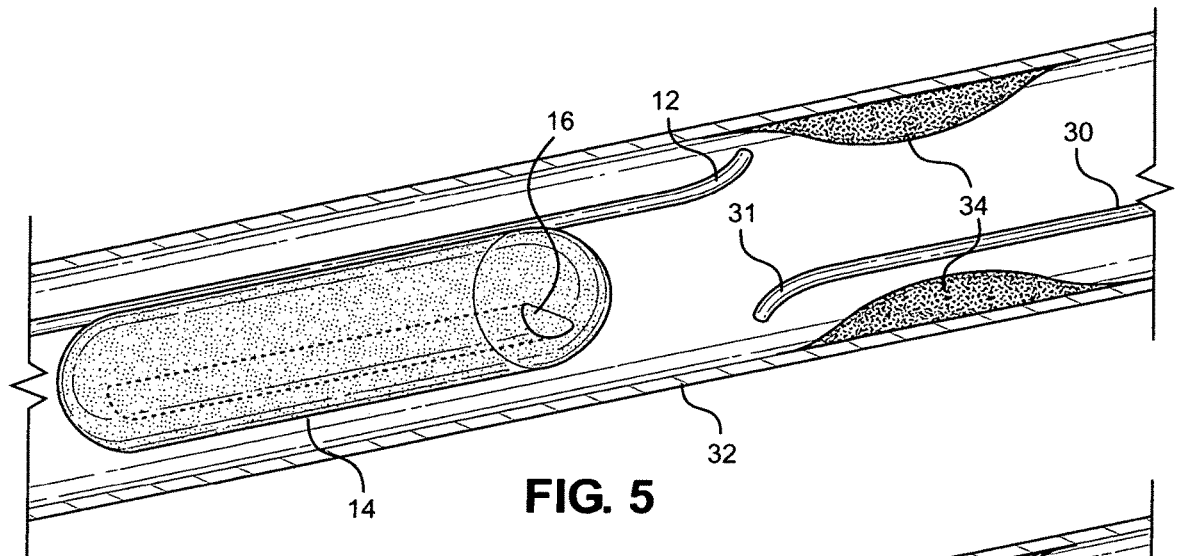
FIGS. 5-7 are schematic views showing the use of the balloon snare of FIGS. 1 & 2 in capturing and moving a retrograde wire in a blood vessel or within a catheter.
Figure 6:
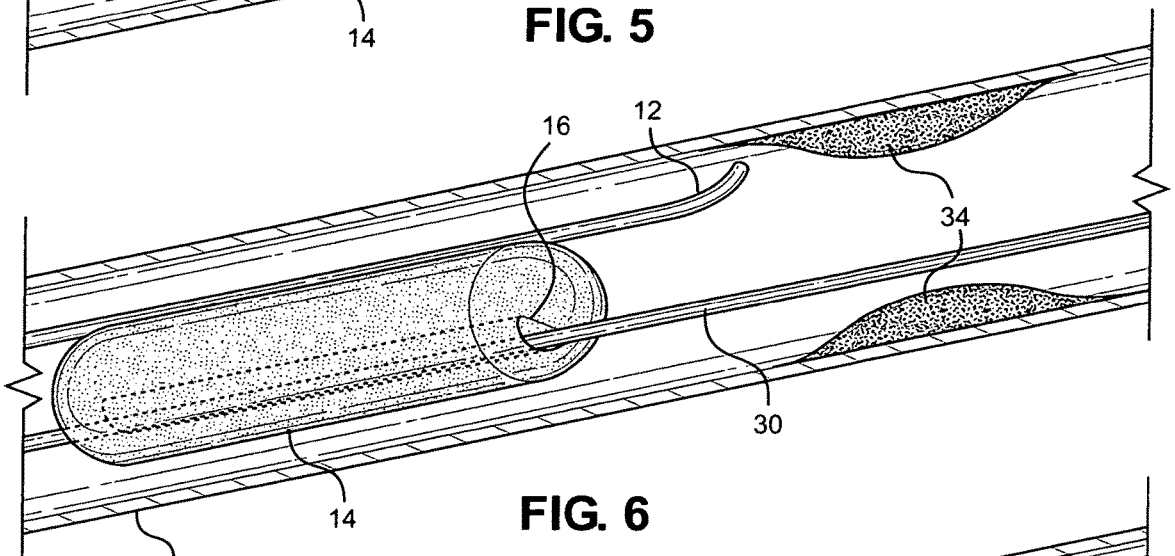
Figure 7:
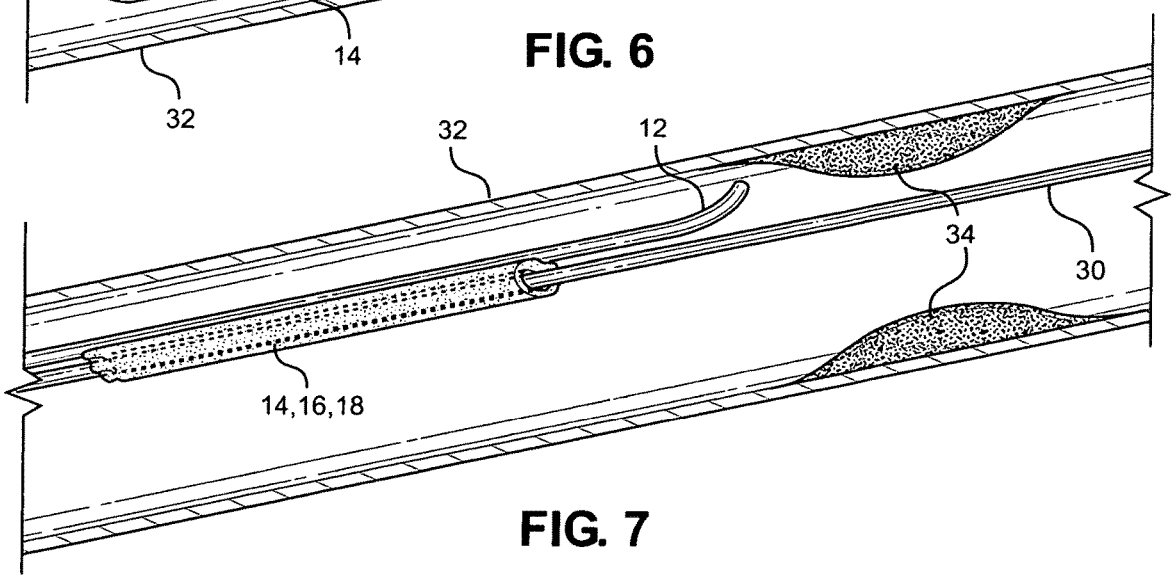

FIGS. 5-7 schematically illustrate a procedure for use of the first embodiment of the snare 10 for capturing and moving a retrograde wire 30 in a blood vessel 32. FIG. 5 shows the antegrade rail wire 12 connected to the balloon 14 used to move the balloon 14 in blood vessel 32 to a stenosis 34 proximal to where an end 31 of the retrograde wire 30 is located. The retrograde wire 30 is advanced/steered into the central lumen 16 of the balloon 14 by using conventional techniques until a significant portion of the wire 30 (including the end 31) is within the lumen 16, preferably—as illustrated in FIG. 6—until the wire 30 passes completely through the lumen 16. At that point in time, as seen in FIG. 7, the balloon 14 is collapsed by deflating it so that it snares the wire 30, gripping it with sufficient force alone to allow the wire 30 within the balloon 14 to be re-positioned within or extracted from the blood vessel 32. If the balloon 14 is removed (not shown) from the blood vessel 32 using the rail wire 12 the retrograde wire 30 comes with it. If the balloon 14 is used merely to re-position the wire 30 then the balloon 14 is inflated again when the wire 30 is at its desired location and the balloon 14 alone is then removed.

While FIG. 5 shows moving the balloon 14 in a blood vessel 32 while in inflated condition, under some circumstances the balloon 14 may be inserted in deflated condition and inflated at a location within the blood vessel 32.

The soft material exterior of the balloon 14 protects the interior walls of the blood vessel 32 from being damaged by the retrograde wire 30 during re-positioning or extraction, and the snare 10 is easier to manipulate than many conventional wire snares. Also, the balloon's ability to obstruct the vessel (e. g. blood vessel) lumen allows easy direction of the material or wire to the only available path: the balloon's lumen 16 or cavity 29.

While the balloon snare of the invention is particularly applicable to the re-positioning or removal of retrograde wires from blood vessels the same basic procedure can be utilized to remove or re-position other objects from or within blood vessels, or other human or animal body parts or catheters within a body part, including, but not limited to, the gastrointestinal tract lumen, or any ducts, fistulas, or tubular lumen within a human or animal body.

The invention is to be accorded the broadest interpretation of the claims limited only by the prior art, so as to encompass all equivalent devices and methods. Also, all specific smaller ranges within an indicated range are specifically encompassed hereby.

What is claimed is:

1. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, wherein the balloon has a cross-sectional area, including the lumen or cavity, of about 1-80 mm$^2$ and approximately the same length as the lumen or cavity.

2. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, wherein the balloon lumen or cavity comprises a central elongated lumen defined by the biocompatible semi-compliant plastic material, and wherein the central elongated lumen has a cross-sectional area of about 0.005-0.50 in$^2$, and a length of about 1-600 mm.

3. A snare as recited in claim 2 wherein the balloon has a cross-sectional area, including the lumen, of about 1-80 mm$^2$, and is approximately the same length as the central elongated lumen.

4. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, wherein the balloon lumen or cavity comprises a central elongated lumen defined by the biocompatible semi-compliant plastic material, and wherein the central elongated lumen has a cross-sectional shape comprising a modified crescent.

5. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, wherein the rail wire is an antigrade rail wire operatively connected to the balloon by a biocompatible adhesive or stitching.

6. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, wherein the balloon lumen or cavity comprises a central elongated lumen defined by the biocompatible semi-compliant plastic material, and wherein the material defining the central elongated lumen includes a hydrophilic or hydrophobic interior coating.

7. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, wherein said wire is operatively connected to an outer surface of said balloon by stitching.

8. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, wherein the balloon lumen or cavity comprises a central elongated lumen defined by the biocompatible semi-compliant plastic material, and wherein the material defining said central elongated lumen includes a hydrophobic interior coating.

9. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, and a retrograde wire captured within said lumen or cavity.

10. A snare consisting essentially of:
   a wire;
   an inflatable/collapsible balloon of biocompatible semi-compliant resilient plastic material operatively connected to said wire; and
   a lumen defined within the balloon providing for the capture of an object within the lumen when the balloon is deflated so that the balloon by itself sufficiently snares the object to allow movement of the object with the balloon.

11. A snare comprising a rail wire operatively connected to an inflatable/collapsible elongated balloon of biocompatible semi-compliant resilient plastic material and an elongated lumen or cavity defined by or within the elongated balloon providing for the capture of an object within the elongated lumen or cavity when the balloon is deflated so that the elongated balloon by itself sufficiently snares the object to allow movement of the object with the elongated balloon, and wherein said elongated balloon has first and second ends and wherein said wire operatively connected to said elongated balloon extends both between and past both said first and second ends thereof.

* * * * *